United States Patent [19]

Brown

[11] Patent Number: 5,234,829

[45] Date of Patent: Aug. 10, 1993

[54] PURIFICATION METHOD FOR MATERIALS HAVING NICK TRANSLATION ABILITY

[75] Inventor: William E. Brown, Pittsburgh, Pa.

[73] Assignee: Carnegie Mellon University, Pittsburgh, Pa.

[21] Appl. No.: 584,437

[22] Filed: Sep. 13, 1990

Related U.S. Application Data

[60] Continuation of Ser. No. 128,708, Dec. 4, 1987, abandoned, which is a division of Ser. No. 638,638, Aug. 7, 1984, Pat. No. 4,767,708.

[51] Int. Cl.$^5$ .............................................. C12N 9/12
[52] U.S. Cl. ................................. 435/194; 435/815; 435/816
[58] Field of Search ...................... 435/194, 815, 816

[56] References Cited

U.S. PATENT DOCUMENTS

| | | | |
|---|---|---|---|
| 4,468,464 | 8/1984 | Cohen et al. | 435/317 |
| 4,563,424 | 1/1986 | Riggs | 435/71 |
| 4,704,362 | 11/1987 | Itakura et al. | 435/253 |
| 4,767,708 | 8/1988 | Minkley et al. | 435/194 |

OTHER PUBLICATIONS

Minkley, E. G., et al. (1984) J. Biol. Chem 259(16), 10386-10392.
Kitayama, S., et al. (1977) Biochim. Biophys. Acta 475, 23-31.
Chang, L. M. S. et al. (1984) J. Biol. Chem. 259(23), 14679-14687.
Bekkering-Kuylaars, S. A. M., et al. (1972) Biochim. Biophys. Acta 272, 526-538.
Freifelder, D. (1982) Physical Biochemistry, 2d Ed., W. H. Freeman and Co., pp. 270-272.
Kelly, W. S., et al. (1979) J. Biol. Chem. 254(9), 3206-3210.
C. M. Joyce and N. D. F. Grindley, Proc. Natl. Acad. Sci. U.S.A. 80, 1830 (1983).
A. Sparos and S. G. Sedgwick, Current Genetics 8, 333 (1984).
T. Maniatis, E. F. Fritsch and J. Sambrook, Molecular Cloning, A Laboratory Manual, 108-112 (1982).
C. M. Joyce et al., J. Biol. Chem., 257(4) 1958 (1982).
D. Raibaud et al., J. Mol. Biol., 163, 395 (1983).
W. T. McAllister et al., J. Mol. Biol., 153, 527 (1981).
L. A. Loeb, Eurcaryotic DNA Polymerase in "The Enzyme", 3rd. ed. P. D. Boyer, ed., Academic Press, New York 1974, pp. 174-188.
D. F. Ward and N. E. Murray, J. Bacteriol., 142(3), 962 (1980).
A. Kornberg, DNA Replication, W. H. Freeman & Co., San Francisco, 1980, pp. 169-205; 514-523.
G. S. Stent et al., Molecular Genetics; An Introductory Narrative, 2d ed. (1978) p. 623.
P. Lopez et al., J. Bacteriol., 169(10), 4869 (1987).
B. D. Davis et al., Microbiology, 3d ed. Harper & Row (1980) p. 139.
J. J. Dunn & F. W. Studier, J. Mol. Biol., 166, 477 (1983).
S. Martinez et al., GENE, 44, 79 (1986).

Primary Examiner—Charles L. Patterson, Jr.
Attorney, Agent, or Firm—Reed Smith Shaw & McClay

[57] ABSTRACT

The present invention pertains to a method of purification of DNA polymerase I, and the polymerase and Nick-translation activities thereof. In one embodiment, the method of purification is directed to circumstances where there are amplified amounts of the same relative to that which is found naturally occurring. In another embodiment, the purification method is directed to shortening the time period for the purification of the same whether in an amplified amount or not as compared to the time taught in the prior art.

5 Claims, 4 Drawing Sheets

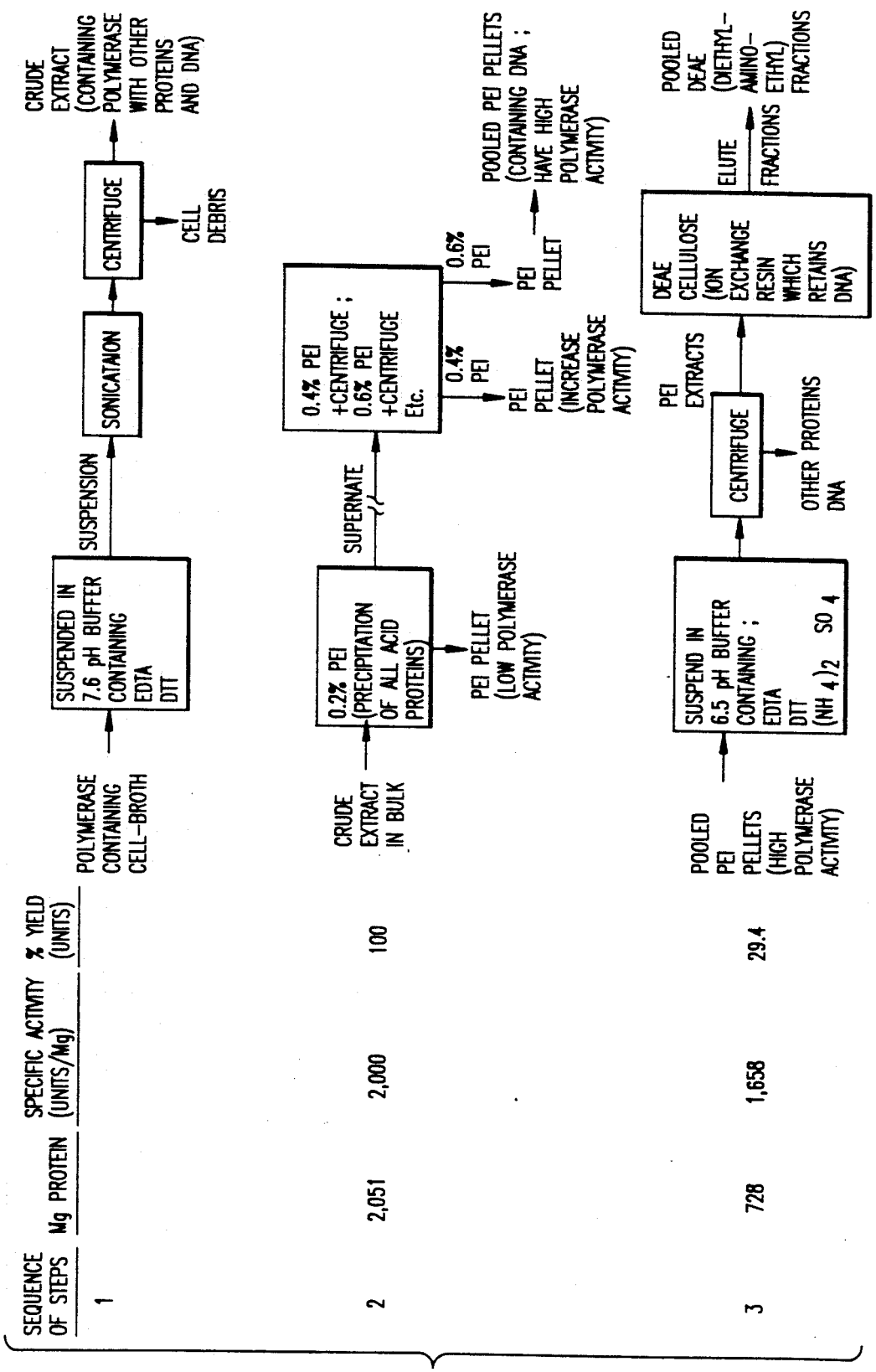

PURIFICATION METHOD FOR MATERIALS HAVING NICK TRANSLATION ABILITY

This invention was made under National Institutes of Health grants 5ROI GM 28925 and 5ROI GM 24688.

The present invention is a continuation of U.S. Patent application Ser. No. 07/128,708, filed Dec. 4, 1987, now abandoned, which is a divisional patent application of Ser. No. 06/638,638 filed Aug. 7, 1984, now U.S. Pat. No. 4,767,708.

GENERAL DESCRIPTION OF THE INVENTION

This invention relates to novel recombinant plasmids for the enhanced expression of an enzyme, to the preparation by gene cloning of such plasmids, to bacterial strains containing said plasmids, to methods for the conditional control of the expression of said enzyme and a method for the purification of said enzyme.

The prior art has failed to clone polA, the structural gene which codes for DNA polymerase I (Pol I), onto a multicopy plasmid because the resultant increase above the natural level of expression of Pol I was known to be lethal to a host bacterium (Kelley, W. S., Chalmers, K. and Murray, N.E. (1977), *Proc. Natl. Acad. Sci. U.S.A.* 74, 5632–5636). In accordance with the present invention a novel recombinant plasmid has been developed and transformed into a host bacterium (*E. coli*) to produce a strain whose expression of DNA polymerase I is subject to experimental control. Growth conditions are selected to enable the host to express conditionally a greatly enchanced level of DNA polymerase I, even though a lesser enhancement of this enzyme is normally lethal to the host. The growth control conditions produce a broth which is benefited by an improved DNA polymerase I purification scheme. Through the improved purification scheme, Pol I is recovered in relatively high yields of greater purity (specific activity) and stability and with relatively short purification time requirements as compared to prior art purification methods.

The novel recombinant plasmid for the production of DNA polymerase I is plasmid pMP5. The viable *E. coli* strain containing this plasmid is ATL100, which was deposited in the American Type Culture Collection Depository on Jun. 29, 1984, under Accession number 39753. The microorganism so deposited is available to the public and will remain so for the life of any patent issuing from this application. The novel plasmid can be separated from the deposited host microorganism by conventional methods known to the art.

An article entitled "Construction of a plasmid that overproduces the large proteolytic fragment (Klenow fragment) of DNA polymerase I of *Escherichia Coli*" by C. M. Joyce and N. D. F. Grindley (1983) *Proc. Natl. Acad. Sci. U.S.A.* 80, pp. 1830–1834, teaches the construction of plasmids which direct the over-production of the carboxyl-terminal two-thirds of DNA polymerase I, known as the Klenow fragment of the enzyme. The Pol I molecule can be split into two enzymatically active fragments, a large fragment and a small fragment. The large or carboxyl-terminal fragment (the Klenow fragment) contains the polymerase and 3'-5' exonuclease functions whereas the smaller fragment contains the 5'-3' exonuclease activity necessary for the nick-translation reaction of Pol I.

The article by Kelley, Chalmers and Murray teaches that the polA gene could not be stably maintained on a multicopy plasmid. Therefore, Joyce and Grindley began their construction with a mutation of the polA gene located amino terminal to the Klenow fragment coding region. The polA gene was then further mutated by the removal of the portion of the gene upstream of the Klenow fragment so that the promoter was by necessity also removed with the gene fragment. The remaining portion of the polA gene, containing the coding region for the Klenow fragment, was fused to translational control signals and cloned downstream of a lac or phage lambda promoter, both of which are more active than the natural promoter of the polA gene. Thereby, a plasmid was produced capable of overproducing only the Klenow fragment of the Pol I molecule.

The present invention is directed to a novel plasmid containing the entire nonmutated structural gene coding region for the production of the complete Pol I enzyme, including both the Klenow fragment and the smaller fragment. As stated above, the smaller fragment is necessary for the nick-translation reaction of Pol I. The nick-translation reaction of Pol I is an extremely useful reaction because it is universally used to insert into DNA selected nucleotide bases which are radioactively or otherwise tagged and serve as DNA probes. DNA probe-based diagnostics for cytomegalovirus, Epstein-Barr virus, hepatitis B virus and herpes virus are currently being produced commercially for scientific and medical laboratories.

The novel plasmid of the present invention contains the entire and undamaged polA gene coding region enzymatically excised from a DNA molecule. However, it is an important feature of this invention that the cloned polA gene fragment contains essentially none of or at the most only a portion of the activity of its natural promoter. For instance, the natural promoter could be rendered less active by removing at least a portion thereof or by introducing the novel plasmid into a heterologous host where the natural promoter has reduced activity. The promoter is a transcriptional control element in a DNA molecule that regulates the expression of the gene and is adjacent to the gene. The cloned polA gene is fused enzymatically to a foreign promoter whose activity is subject to conditional control and which will be less active than the natural polA promoter under environmental conditions where the foreign promoter is in its non-activated state. We have discovered that the restriction enzyme BglII will cut within the polA promoter sequence and severely damage it. This is a significant discovery of the present invention, since it eliminates or greatly reduces the unregulated expression of Pol I, which would otherwise be lethal to the cell. Had this not been the case, BglII cutting of polA DNA could have been used, followed by treatment with exonuclease BAL-31 to inactivate the polA promoter. An exonuclease such as BAL-31 will carry out step-wise removal of individual nucleotides, eventually giving removal of all or part of the natural promoter. Examples of tightly controllable and potentially more active foreign promoters include the lac promoter, the trp promoter and the leftward promoter $P_L$ of phage lambda, all of which are subject to "negative" or repressible control. If desired, the foreign promoter can be subject to "positive" or activator control. Examples of such promoters are the mal promoter and the late promoters of bacteriophage $T_7$. The active promoter can be native to the vector plasmid or can be cloned into the vector plasmid from a foreign source.

When a plasmid chimera containing the cloned complete and undamaged polA gene coding region with at least a portion of its natural promoter removed and provided with a foreign and more powerful promoter is transformed into a host bacterium, the plasmid tends to express an amount of Pol I which is lethal to the host strain or at least inhibitory of cell growth in the host strain. In general, the expression of Pol I above the natural amount is lethal, debilitating or inhibitory to cell growth in a host stain. However, as indicated above, the foreign promoter can be chosen such that its activity is subject to conditional control. Therefore, when the host bacterium receives the novel plasmid of this invention it is maintained under environmental conditions which fail to activate or which "repress" substantially entirely, or to a major extent, the activity of the promoter and under which the cells can multiply substantially normally to produce an enlarged population of cells in which the novel plasmid is replicated.

While continuing to repress the foreign promoter, or in the case of a positively regulated promoter not inducing activation of the activity of the foreign promoter, the cells are cultured in a nutrient broth to induce cell multiplication and produce an enlarged cell population containing the replicated novel plasmid. This cell multiplication occurs essentially without an enhanced expression of Pol I. Thereupon, the conditions of promoter repression are "switched" off or the conditions of activation are switched "on", and the foreign promoter is permitted to influence the polA gene to express an enhanced yield of Pol I. After a limited period of such expression, the cells die or become delibitated or growth inhibited. The only surviving or multiplying cells are a subpopulation of natural mutants which do not express an excess quantity of the enzyme. Because of the enlargement of the culture containing the replicated novel plasmid, and the enhanced level of polA expression resulting from the induction of the foreign promoter, the harvestable amount of DNA polymerase I produced by an E. coli host is about 138 times the amount of Pol I produced by wild type E. coli K12. This degree of amplification is remarkable when compared to the current commercial source of Pol I, strain CM5199, which is typically capable of only a 17-fold amplification over wild type K12.

The present invention can be performed using temperature as the environmental factor which controls expression of Pol I. For example, a polA coding region can be cloned downstream from the leftward $P_L$ promoter of phage lambda, and control over $P_L$ activity then provided via a temperature sensitive phage lambda cI gene product (repressor). In this case, the cell colony is cultured in a nutrient broth at a temperature equal to or below 32° C., at which temperature expression of polymerase is repressed, but the cell colony grows. After the cell colony has grown sufficiently, the temperature "switch" can be changed to 42° C., at which temperature a high yield of Pol I is expressed until the cells stop growing after about 40 minutes. Examples of other environmental factors that can be employed include osmotic pressure and chemical inducers of derepression, each of which can be employed as an on and off mechanism analogous to the temperature switch. An example of a chemical inducer is IPTG (isopropyl-$\beta$-D-thiogalatopyranoside), which binds to and turns "off" the lac repressor. A positively regulated promoter can also be turned off and on by environmental factors. Examples are the mal promoter which can be switched on by the addition of the carbohydrate maltose to the growth medium, and the late promoters of bacteriophage T7 which are utilized only by the virus' own RNA polymerase. T7 RNA polymerase can be provided by infecting cells with the virus or by co-cloning of its gene under conditions where it too is subject to conditional control.

This invention can be applied in a similar manner to plasmids containing a whole undamaged structural gene coding region for an enzyme or protein other than Pol I having its natural promoter partially or entirely removed or otherwise rendered inactive and which is fused to a tightly regulated foreign promoter. This invention will be of utility specifically in those instances, such as with polA, where expression from the natural promoter of the gene of interest is not tightly regulated and where cloning of the intact structural gene onto a high copy number plasmid is impossible because of a lethal or debilitating overproduction of the corresponding gene product. Such other plasmids can be transformed into a host microorganism, such as E. coli, and cultured in a nutrient broth in which they multiply and replicate the plasmid under the influence of an active repressor or an inactive activator for the foreign promoter. When the lambda leftward promoter is used an effective repressor is the temperature sensitive cI857 repressor. This repressor is of a type which can be "switched" off by temperature inactivation after the culture has grown to allow the enlarged cell population within which expression of the enzyme from the cloned gene is induced to effect a yield of the cloned gene's product which is greatly enhanced compared to the wild type yield and which would be lethal, debilitating or growth inhibiting to the host.

We have developed a novel method for the purification of Pol I produced by the method of this invention, which is capable of harvesting 10 to 15 weight percent of the available Pol I in a period of about 2½ days, which is both a high recoverable yield and a short purification duration compared to prior methods. For example, present separating procedures require about a week. The novel method is applied to the bulk crude extract, rather than to aliquot portions.

A novel feature of the present purification method is the removal of DNA prior to salt precipitation of Pol I. It is known that in the presence of a high level of DNA, protein remains suspended in high salt precipitations and must be filtered because it does not effectively pellet out by centrifugation. We have discovered that if DNA is removed prior to high salt precipitation of Pol I, the Pol I is effectively recovered as a pellet by centrifugation.

A crude extract can be prepared for the novel purification method by sonication of the polymerase-containing cell suspension in bulk followed by centrifuging to remove cell debris, yielding a supernate containing DNA polymerase I, together with other proteins and DNA. In the present system, some DNA precipitates with protein in the polyethyleneimine precipitation step. It is a novel feature of this purification method that this DNA is removed by means of an ion exchange resin, which retains DNA, in advance of the salt precipitation steps of the procedure. Since DNA is negatively charged, it adheres to an ion exchange resin having positive charges. If the DNA is not removed prior to these salt precipitation steps and a significant quantity of DNA is present, the polymerase will remain suspended during the high salt precipitation step and will not be removable as a pellet in the centrifugation operation following the high salt precipitation step. Although the suspension can be removed by filtration, it is an advantageous feature of the present procedure that centrifugation can remove the polymerase as a pellet, as described in the following procedure.

The DNA polymerase I purification method of this invention comprises in sequence:

(a) subjecting the crude extract to a series of treatments with polyethyleneimine each followed by centrifuging with the polyethyleneimine being present in increasing concentrations in the series of steps to precipitate acidic proteins together with some DNA and form polyethyleneimine pellets containing various concentrations of polymerase activity (units/mg);

(b) extraction of the polyethyleneimine pellets of relatively high polymerase activity with a buffer and contacting said soluble polyethyleneimine pellet extracts with an ion exchange resin such as diethylaminoethyl cellulose, which retains DNA, and recovering an eluate having DNA removed;

(c) treating said eluate having DNA removed with a salt for the precipitation of proteins in relatively low concentration and centrifuging to produce a supernate, and then treating the supernate with the salt in a relatively high concentration and centrifuging to produce a protein pellet, the salt used being ammonium sulfate, preferably, and calcium chloride, less preferably;

(d) dissolve said protein pellet in a buffer followed by dialysis to remove salt from protein; and (e) passing said soluble dialyzed protein over an ion exchange resin for the retention of DNA polymerase I and subsequently deionizing said resin to recover ion exchange fractions of high polymerase activity. These fractions are the high activity DNA polymerase product of the procedure.

An outline of the polymerase purification procedure is presented in FIG. 3.

Prior purification methods for the recovery of polymerase from a system wherein it has been amplified have encountered considerable difficulty because while the polymerase is being greatly amplified, nucleic acids and other proteins are also being amplified making the purification of the polymerase very difficult. It is an important feature of the present system that the DNA is removed from the system before the polymerase salt precipitation step. When the present Pol I amplification method is combined with the present purification method, the recovered polymerase has a higher specific activity than any yet reported, i.e. 32,000 units/mg vs. 18,000 units/mg for the prior art.

DESCRIPTION OF THE PREFERRED EMBODIMENTS

This following discloses the construction of plasmid pMP5 which contains both the coding sequence for DNA polymerase I with a damaged polA promoter, and the bacteriophage lambda $p_L$ promoter for conditional control of the polA gene expression. Transformation of pMP5 into E. coli N4830 yields strain ATL100 which under inducing conditions provides a 138 fold amplification of DNA polerase I.

The plasmid pMP5 was constructed as a derivative of the $p_L$ expression vector pHUB2 (Bernard H.-U. Remault, E. Hershfield, M. V., Yanofsky, C., and Franklin, N. (1979) Gene 5, 59-76) using the transducing phage NM825 (Murray, N. E., and Kelley, W. S. (1979) Mol. Gen. Genet. 175, 77-87) as a source of polA+.

pHUB2 DNA was digested with BamHI and SalI and ligated to DNA of NM825 cut with BglII and SalI (FIG. 1) This DNA was transformed into strain XK603 and kanamycin-resistant, tetracycline-sensitive clones identified. Strains containing apparent inserts into pHUB2 were assayed for DNA polymerase I levels after growth and heat induction of expression from $p_L$. Strain XK603 contains a heat-inducible lambda prophage whose cI857[Ts] repressor gene provides the conditional control over the plasmid's $p_L$ promoter. The plasmid pMP5 was detected by its ability to greatly overproduce DNA polymerase activity upon temperature inactivation of the resident phage cI857 repressor and the purified plasmid DNA had the expected size and restriction endonuclease cleavage pattern. Strain ATL100 was constructed by transforming plasmid pMP5 into E. coli strain N4830 with selection for kanamycin resistance. Strain N4830 contains a defective lambda prophage, including a cI857[Ts] gene, and gives constitutive expression of the lambda N gene product at the inducing temperature (Gottesman, M.E., Adhya, S. and Das, A. (1980), J. Mol. Biol. 140, 57-75).

Growth of ATL100—A standing overnight culture of ATL100 at 28° C. was started by inoculating 15 ml of L broth (L broth contains per liter: 10 g tryptone, 5 g yeast extract, 10 g NaCl) containing 50 μg/ml kanamycin and 0.2% glucose with a 1 ml frozen sample of ATL100 that was previously prepared from a culture showing a high ratio of small to large colony formation. Under these growth conditions the 15 ml overnight culture routinely grew to a Klett value of 100 in a 24 hr period. A second overnight culture was then started in L broth containing kanamycin and 0.2% glucose by inoculating 3×500 ml cultures each with 5 ml from the previous standing overnight culture and allowing these to grow at 28° C. with slow shaking (approx. 90 rpm) to a Klett value of 100. The 3×500 ml cultures were then used to inoculate a 28 L fermentor (New Brunswick Microferm) containing 20 l of L broth with kanamycin and 0.2% glucose. The cells were grown at 28° C. until they reached a Klett value of 100 at which time a slow temperature induction was started by increasing the temperature to 42° C. over a 40 min. interval. The culture was then allowed to grow at 42° C. for an additional 10 min. Fifty minutes after the start of induction, the fermentor was quickly chilled to 20° C. and the cells harvested by centrifugation. The cell paste was collected and stored frozen at −50° C.

Polymerase Purification—All steps of the purification are carried out at 4° C. Frozen cells, stored at −50° C., are thawed and resuspended (3-4 ml/gm cells) in 50 mM Tris-Cl, pH 7.6, buffer containing 2 mM EDTA and 1 mM dithiothreitol (DTT). The suspension is sonicated in a Bronson Sonifier, Cell Disrupter 200, at a setting of 10 for 5 minute pulses with the sonication vessel immersed in an ice water bath. Absorbance of the suspension is monitored at 550 nm to determine the extent of lysis after each pulse. Generally, maximal lysis required 15-20 minutes total sonication. The final suspension is centrifuged at 17,300×G for twenty minutes. The supernate is designated as the crude extract.

Polymin P titration—A 10% (v/v) solution of Polyethyleneimine (Polymin P, PEI (Miles Laboratories)), titrated to pH 7.6 is added to the supernate to a final concentration of 0.2%. The suspension is allowed to stand 30 minutes at 4° C. and centrifuged at 17,300×G for 15 minutes. The pellet is saved and the PEI concentration of the supernate is raised to 0.4%. After 30 minutes the suspension is again centrifuged, the pellet saved, and the procedure repeated at 0.2% PEI intervals until the supernate remains clear after PEI addition. All pellets arE saved at −20° C. until polymerase assays are performed on aliquots from each of the individual PEI supernates saved during the titration.

DEAE-Cellulose Chromatography—PEI pellets containing the maximum polymerase activity are combined, resuspended in one-third the original volume of a buffer containing 20 mM K.PO$_4$, pH 6.5, 2 mM EDTA, 2 mM DTT, and 0.2M (NH$_4$)$_2$SO$_4$. The suspension is homogenized and centrifuged at 17,300×G for 15 minutes at 4° C. The extraction is repeated twice more and the supernates are combined and designated as the PEI resuspension (Table 1). This resuspension is loaded directly onto a 5×30 cm DEAE-Cellulose (DE-52, Whatman) column equilibrated and run in a 0.2M K.PO$_4$, pH 6.5 buffer containing 1 mM DTT. Under these conditions, pol I elutes from the column in the breakthrough volume. The absorbance at 280 and 260 nm is measured and fractions with a 280/260 ratio greater than 1.0 are combined. Using this criterium, pol I assays of DEAE fractions from several preparations have shown that greater than 90% of the pol activity is recovered from the column in these fractions. This sample is designated as the pooled DEAE fractions (Table 1).

Ammonium Sulfate Fractionation—The pooled DEAE fractions are brought to 40% saturation in (NH$_4$)$_2$SO$_4$ at 4° C., allowed to equilibrate 30 minutes and centrifuged at 17,300×G for 15 minutes. The supernate is raised to 80% saturation in (NH$_4$)$_2$SO$_4$ at 4° C., allowed to stand 2-3 hours, and centrifuged at 17,300×G for 15 minutes. At this point the pellet can be saved frozen at −20° C.

Bio-Rex 70 Chromatography—The 80% (NH$_4$)$_2$SO$_4$ pellet is resuspended in a 100 mM K.PO$_4$, pH 7.0, buffer containing 1 mM DTT, and dialyzed against 2×2 liter changes in the same buffer for 2 hours total. The dialyzed, resuspended pellets are adjusted to the conductivity of the column buffer with cold deionized water and loaded onto a 2.5×15 cm Bio-Rex 70 (Bio-Rad) column equilibrated in 50 mM K.PO$_4$ pH 7.0, buffer containing 1 mM DTT. The column is washed until the absorbance at 280 nm returns to baseline following the flow-through material and then a linear gradient to 0.5M NaCl in 50 mM K.PO$_4$, pH 7.0, buffer containing 1 mM DTT (600 ml total volume) is applied. Fractions (12 ml/fraction) are monitored for absorbance at 280 nm, conductivity, and polymerase activity. A 10% SDS polyacrylamide gel is run on fractions containing polymerase activity and fractions are pooled based on maximum activity and minimum protein contamination. Pooled fractions are stored either at 4° C. with 10 mM DTT or at −50° C. after dilution to 50% glycerol and addition of DTT to 10 mM.

Miscellaneous Methods—DNA polymerase I assays were performed (Kelley, W.S., Chalmers, K., and Murray, N.E. (1977) *Proc. Natl. Acad., Sci. U.S.A.* 74, 5632-5636) using nicked calf thymus DNA (Richardson, C.C. (1966) in *Procedures in Nucleic Acid Research* (Cantoni, G.L. and Davies, D.R. eds.) Vol. 1, pp. 212-223, Harper and Row, New York) or d(AT) copolymers as primer/template. Protein concentration was determined both by the Lowry method (Lowry, O.H. Rosebrough, N.J. Farr, A. L. and Randall, R.J. (1951) *J. Biol. Chem.* 193, 265-275) using bovine serum albumin as the standard, and by quantitative amino acid analysis on a Durrum D-500 analyzer. Protein analysis by electrophoresis was performed on 10% acrylamide gels under reducing conditions in the presence of sodium dodecyl sulfate according to the procedure of Laemmli (Laemmli, U.K. (1970) *Nature* 227, 680-685).

Optimizing expression of DNA polymerase I— Growth of ATL100 is extremely slow at non-inducing temperatures, with a doubling time ($t_D$) of 120 minutes in L broth at 32° C. This is consistent with the strain making very small colonies after overnight growth on L broth plates. Surprisingly, shifting a broth-grown culture of ATL100 to the inducing temperature (42° C.) resulted in a transient cessation of growth followed thereafter by an acceleration of the growth rate until it reached $t_D$ of 60 min. The level of DNA polymerase increased abruptly upon shifting to the inducing temperature, attaining its maximal specific activity within 40 to 50 min. Thereafter, however, polymerase specific activity gradually declined, while the culture continued to grow (FIG. 2).

This rather curious cell growth versus polymerase specific activity behavior led us to plate out samples of the culture from the kinetic experiment for viable counts. It has now been discovered that large-scale cultures of ATL100 actually contain two colony types, one of which is very small after overnight growth, the other larger and more normally sized. A typical large scale growth of ATL100, would show a continual decline in the ratio of small to large colonies. For example, the ratio is approximately 70 after the first overnight incubation, 20 after the second overnight incubation, 9 at the time of induction in the fermentor, and 1 to 2 following 300 minutes of growth after induction. A kinetic experiment using a culture derived from the large colony type showed that such a culture continued to grow after shifting to the inducing temperature ($t_D$ of 60 minutes) but did not produce elevated levels of DNA polymerase. The presence of these two colony types thus explains the observed patterns of cell growth and polymerase specific activity. The small colony type over-produces DNA polymerase and does not grow at the inducing temperature whereas the large colony type is non-producing and, by continuing to grow, dilutes polymerase specific activity when it becomes predominant.

Three independent experiments were made to explore the possible relationship between the ratio of small to large colonies in the uninduced culture, and the level of DNA polymerase I obtained after induction. There was found to be a positive correlation between the two, with a small to large colony ratio of approximately twenty being indicative of a near maximal amplification. We have consistently observed the appearance of the large colony type when working with ATL100, even when we inoculate cultures from purified single colonies of the small variety. Thus, there is a clear implication that pMP5 is only marginally tolerated by N4830 and that during growth and/or maintenance of pMP5-containing strains there is a continual selection of plasmid derivatives which no longer produce DNA polymerase, even under ostensibly non-inducing conditions. For this reason, sub-culturing of ATL100 is avoided, and starter cultures are stored frozen.

Rapid Purification of Pol 1—The purification scheme of this invention both increases the yield and decreases the time of purification over other prior art purification schemes. As stated above, the overall procedure takes two and one-half days and yields 10-15% of the total available polymerase.

Traditionally, the PEI titration is performed on an aliquot of the crude extract to determine the appropriate PEI concentration for precipitation of the bulk material. In contrast, the present titration was performed on the whole crude extract. The individual pellets from each PEI precipitation step were stored frozen at $-20°$ C. while polymerase assays were performed on samples of the individual supernates saved during the titration. Appropriate pellets were then chosen for combination based on the loss of polymerase activity from the corresponding supernatant fraction.

The major change from previous protocols occurs at the next step. It was found that DNA apparently interfers with the high salt $(NH_4)_2SO_4$ fractionation (i.e. the 80% cut remains suspended after centrifugation). Therefore, the step involving DEAE-Cellulose removal of DNA was placed before the $(NH_4)_2SO_4$ fractionation. In this case, the PEI resuspension is placed directly on the DEAE-Cellulose column and 80-90% of the polymerase is eluted from the column before the $A_{280/260}$ ratio drops below 1.0. The DEAE elution is followed directly by ammonium sulfate fractionation which yielded a clear supernate after centrifugation of the 80% cut.

TABLE I

Analysis of Purification Scheme

| SAMPLE | mg PROT.[a] | Spec. Act. (units/mg)[b] | % Yield (units) |
| --- | --- | --- | --- |
| Crude Extract | 2051 | 2,000 | 100[c] |
| PEI Resuspension | 728 | 1,658 | 29.4 |
| Pooled DEAE Fractions | 528 | 2,092 | 26.9 |
| 40% Ammonium Sulfate Supernatant | 368 | 3,647 | 32.7 |
| Dialyzed, Resuspended 80% Amm. Sulf. Pellet | 344 | 3,028 | 25.5 |
| BioRex Fractions | 16.2 | 30,162 | 11.9 |

TABLE I-continued

Analysis of Purification Scheme

| SAMPLE | mg PROT.[a] | Spec. Act. (units/mg)[b] | % Yield (units) |
| --- | --- | --- | --- |
| (42-44) | | | |

[a]Protein concentration determined both by Lowry protein assay (J. Biol. Chem. 193, 265-275) and by quantitative amino acid analysis. Results from these methods differed by less than 10%.
[b]Polymerase activity was determined using nicked calf thymus DNA as substrate (J. Biol. Chem. 275, 1958-1964).
[c]Yield of Pol I from crude extract was arbitrarily set at 100%. $3.1 \times 10^6$ units were measured in the crude extract from 63 grams of cells.

Figure 1:
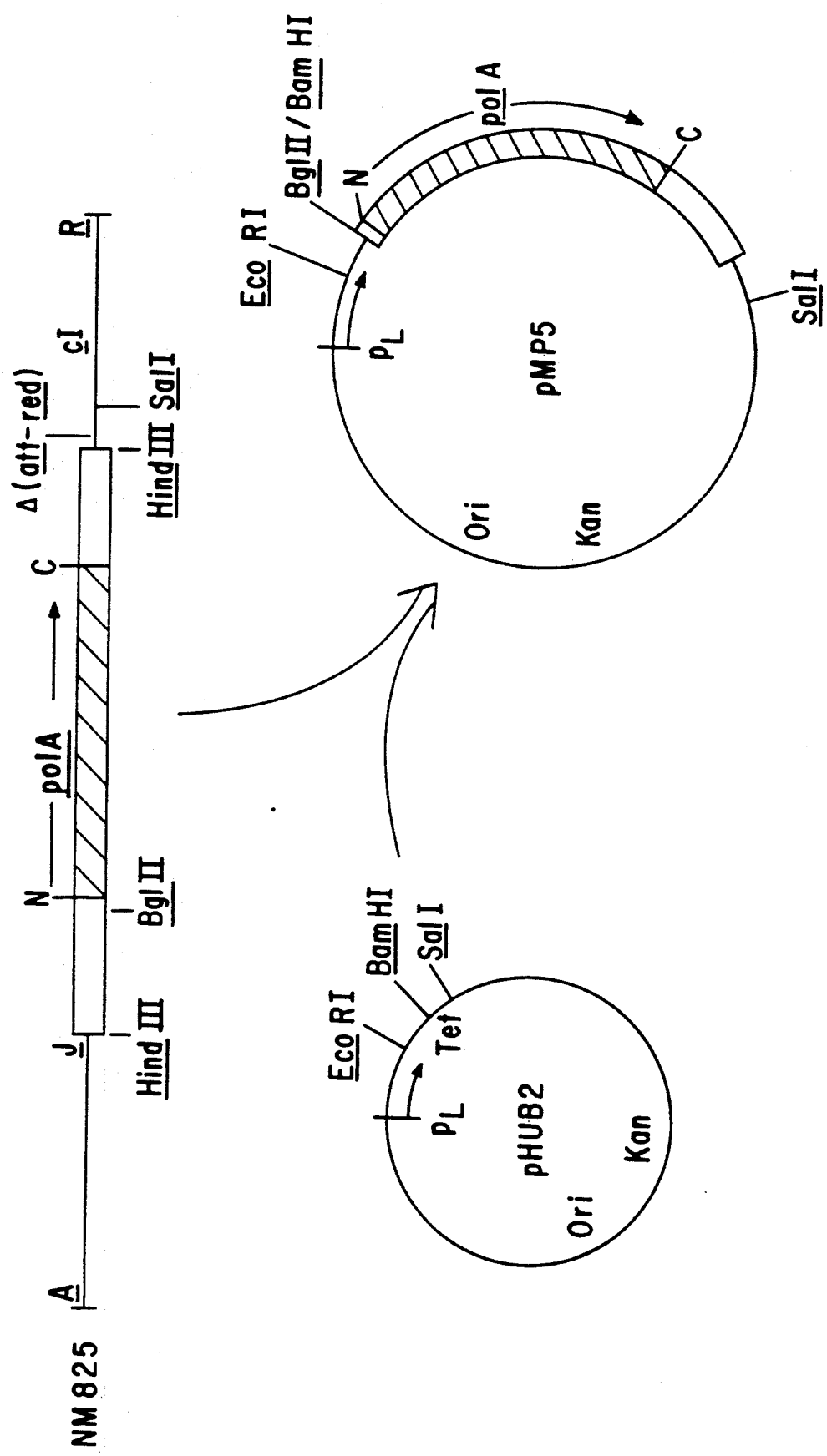
FIG. 1 illustrates cloning of polA+ onto a plasmid expression vector. Phage NM825 carries the polA+ gene (stippled region) in the left-to-right orientation, as indicated by the arrow extending from the amino (N) to the carboxyl (C) terminus. An att-red deletion in the phage vector's right arm brings the right hand HindIII site into close proximity with the lambda SalI site near gam. The expression vector pHUB2 carries the lambda promoter $p_L$ oriented for transcription towards the plasmid's tet gene, as indicated by the arrow.
Figure 2:
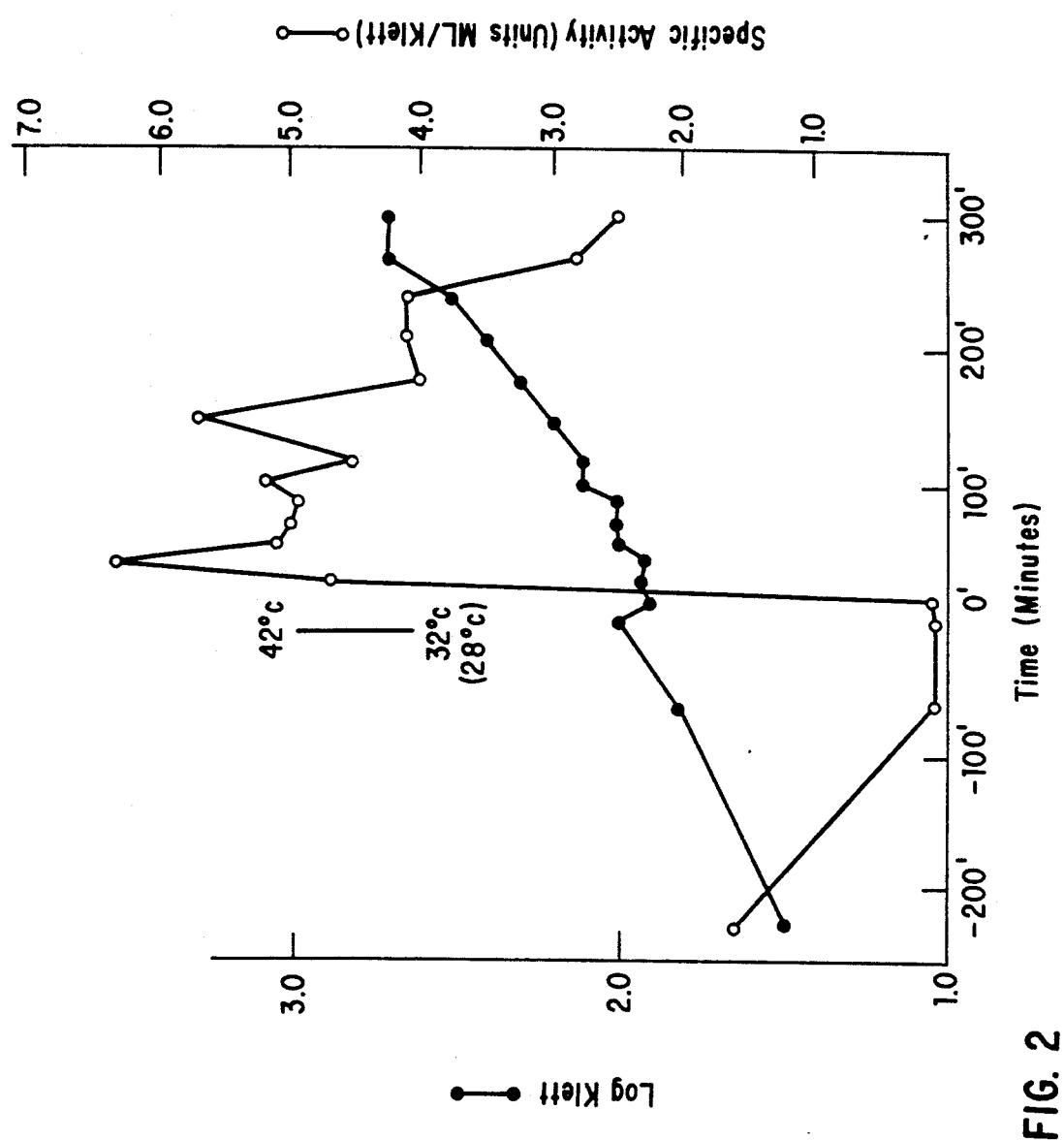
FIG. 2 illustrates growth of and polymerase production from ATL100. Cell density and polymerase specific activity from crude extract aliquots are presented over the time course from 220 minutes prior to induction, through induction at 0 time from either 28° C. or 32° C. to 42° C. to 300 minutes beyond induction. In this case, rapid induction (2° C./min) to 42° C. was performed and cells harvested at 50 minutes from the 28 liter fermenter under these conditions were used in the purification scheme described in Table I.
Figure 3B:
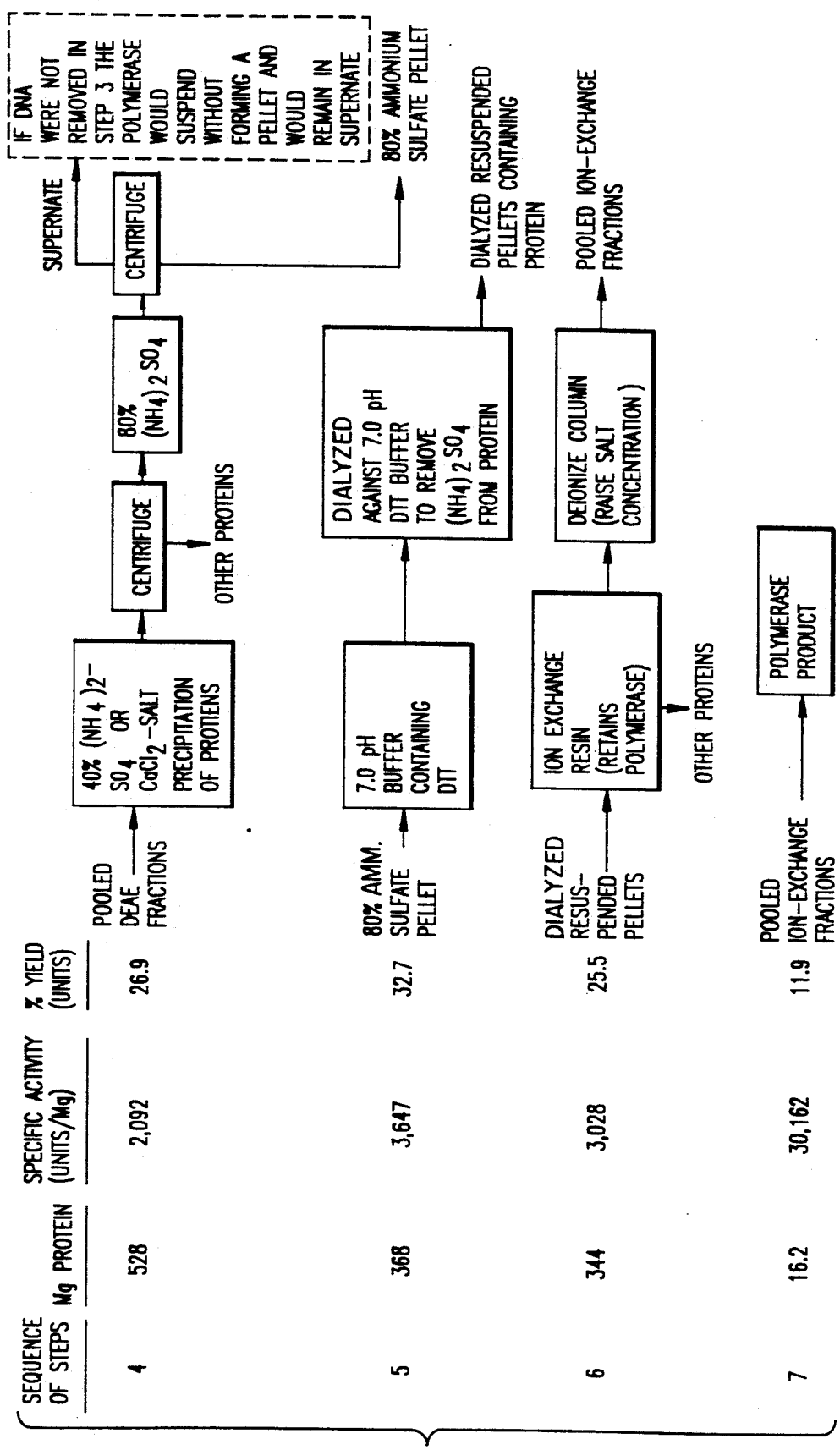

FIGS. 3a and b a schematic diagram illustrating the purification scheme in detail.

We claim:

1. A method for obtaining material having Nick-translation ability from genetically engineered bacterial or yeast host cells which produce the material in an amount greater than they would naturally comprising the steps of:
    placing the genetically engineered host cells which have amounts of material having Nick-translation activity greater than they would have naturally into a container; and
    fractionating the cells to isolate the material having Nick-transaction activity in less than one week wherein said fractionating step includes the steps of:
    a) sonicating the cells to obtain a crude extract;
    b) subjecting said crude extract to a series of treatments with polyethyleneimine each followed by centrifuging with the polyethyleneimine present in increasing concentrations in a series of steps to precipitate acidic proteins in the crude extract and each step forming polyethyleneimine pellets of varying polymerase activity;
    c) extracting polyethyleneimine pellets of relatively high polymerase activity with a buffer and contacting said polyethyleneimine pellet extracts with an ion-exchange resin which retains DNA and recovering an eluate having DNA removed therefrom;
    d) treating said eluate with ammonium sulfate at a concentration that does not precipitate a significant amount of material having Nick-translation activity and centrifuging to produce a supernatant and treating said supernatant with ammonium sulfate at a concentration that precipitates essentially all of the material having Nick-translation activity and centrifuging to produce an ammonium sulfate pellet having said activity;
    e) suspending said ammonium sulfate pellet in a buffer followed by dialysis to remove ammonium sulfate from protein and to produce dialyzed suspended ammonium sulfate pellet containing protein, and
    f) passing said dialyzed suspended ammonium sulfate pellet over a second ion exchange resin which retains the material having Nick-translation activity and subsequently eluting said second resin to obtain ion-exchange fractions of high polymerase activity.

2. A method as described in claim 1 wherein said ion-exchange resin which retains DNA comprises diethylaminoethyl-cellulose.

3. A method as described in claim 2 wherein in step (d), the concentration that does not precipitate a significant amount of material having Nick-translation activity is about 40%; and the concentration that precipitates essentially all of the material having Nick-translation activity is about 80%.

4. A method as described in claim 3 wherein the increasing concentrations of polyethyleneimine in the series of steps in step (b) are 2% increments until the supernatant remains clear after polyethyleneimine addition.

5. A method for purifying an enzyme having DNA polymerase activity in an amount greater than it would naturally, comprising the steps of:

forming a crude extract by sonication of bacteria which have been amplified;

removing DNA from the crude extract by subjecting said crude extract to a series of treatments with polyethyleneimine each followed by centrifuging with the polyethyleneimine present in increasing concentrations in a series of steps to precipitate acidic proteins in the crude extract and form polyethyleneimine pellets of varying polymerase activity;

extracting polyethyleneimine pellets of relativity high polymerase activity with a buffer and contacting said polyethyleneimine pellet extracts with an ion-exchange resin which retains DNA and recovering an eluate having DNA removed therefrom;

precipitating the enzyme into pellets by treating said eluate with ammonium sulfate at a concentration that does not precipitate a significant amount of material having polymerase activity and centrifuging to produce a supernatant and treating said supernatant with ammonium sulfate at a concentration that precipitates essentially all of the material having polymerase activity and centrifuging to produce an ammonium sulfate pellet having said activity;

suspending said ammonium sulfate pellet in a buffer followed by dialysis to remove ammonium sulfate from protein and to produce dialyzed suspended ammonium sulfate pellet containing protein; and passing said dialyzed suspended ammonium sulfate pellet over a second ion exchange resin which retains polymerase material and subsequently eluting said second resin to obtain ion-exchange fractions of high polymerase activity.

* * * * *